United States Patent [19]

Amarasinghe

[11] Patent Number: 4,553,543
[45] Date of Patent: Nov. 19, 1985

[54] SUTURING ASSEMBLY AND METHOD

[76] Inventor: Disamodha C. Amarasinghe, 4068 Bridge Hampton La., Virginia Beach, Va. 23455

[21] Appl. No.: 586,473

[22] Filed: Mar. 5, 1984

[51] Int. Cl.⁴ .............................................. A61B 17/04
[52] U.S. Cl. ................................. 128/334 R; 128/340
[58] Field of Search ............ 128/339, 340, 337, 335.5, 128/335, 334 C, 334 R, 330, 336; 223/102, 103; 112/227

[56] References Cited

U.S. PATENT DOCUMENTS

| | | | |
|---|---|---|---|
| 1,577,054 | 3/1926 | Berkmann | 128/340 |
| 3,265,069 | 8/1966 | Healey, Jr. et al. | 128/334 |
| 3,587,115 | 6/1971 | Shiley | 3/1 |
| 4,103,690 | 8/1978 | Harris | 128/334 R X |
| 4,182,339 | 1/1980 | Hardy, Jr. | 128/334 |
| 4,306,561 | 12/1981 | de Medinaceli | 128/303 |
| 4,310,115 | 1/1982 | Inoue | 128/334 R X |
| 4,345,600 | 8/1982 | Rothfuss | 128/346 X |
| 4,352,358 | 10/1982 | Angelchik | 128/334 |

Primary Examiner—Michael H. Thaler
Attorney, Agent, or Firm—Griffin, Branigan, & Butler

[57] ABSTRACT

A slotted, partially-flared, cylindrically shaped core 12 is mounted inside a tubularly-shaped sleeve 20 with a flared end portion 16 extending out the end of the sleeve 20. A flexible needle 24, which is longer than either the core or the sleeve, is held in each of the core slots 18 by the sleeve, but is allowed freedom of longitudinal movement. Threads 32 attached to the needles are inserted through a wall of a tubular body duct by inserting the flared end portion of the core into the body duct and then forcing the needles to move longitudinally in the slots against the flared end portion so that they bend radially outwardly through the walls of the body duct.

11 Claims, 7 Drawing Figures

SUTURING ASSEMBLY AND METHOD

BACKGROUND OF THE INVENTION

This invention relates generally to the art of surgical suturing, and more particularly, to the art of anastomosing tubularly shaped body ducts, one to another, especially blood vessels.

When performing heart surgery, and other surgery involving blood vessels and other body ducts, the job of anastomosing one vessel to another is normally laboriously performed by stitching edges of blood vessel openings together. This procedure, because the blood vessels are so small and delicate, often takes hours to complete. Although numerous devices have been suggested for expediting this procedure, it is not thought that any of these devices have achieved widespread usage. Many of these devices employ staples, clamps and the like which some surgeons do not like to leave in a body. Many surgeons believe that conventional thread-type, handmade, sutures are preferable over staples and the like.

It is an object of this invention to provide an assembly and method for performing body vessel anastomosis in a relatively rapid manner, thereby reducing the time required for such procedures.

It is a further object of this invention to provide such an assembly which is relatively easy and inexpensive to manufacture, but yet which is straightforward and easy to use.

Still another object of the invention is to provide such an assembly and method for performing body vessel anastomsis which produces standard, thread-type, sutures of a type produced by "hand sewing".

SUMMARY

According to principles of this invention, a plurality of flexible suture needles are held in slots in a flared core by a sleeve which extends about the flexible suture needles and the core. The suture needles, and attached threads, are caused to penetrate the walls by a body duct, such as a blood vessel, by inserting the flared end of the core into the severed body duct and then forcing the needles to move longitudinally in the slots against the flared end of the core so that they bend outwardly and are driven through the wall of the duct. In a preferred embodiment of the invention, the sleeve is constructed of a plurality of separable parts which are separated to release the needles and suture thread from the core and sleeve once the needles have passed through the duct wall.

In one embodiment, suture threads having needles at opposite ends thereof are mounted in oppositely-directed suturing assemblies of this invention so that the needles at the opposite ends of the threads can be passed through walls of two body ducts to be sewn together.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refers to the same parts throughout the different views. The drawings are not necessarily to scale, emphasis instead being placed upon illustrating principles of the invention in a clear manner.

DESCRIPTION OF PREFERRED EMBODIMENTS

Figure 1:
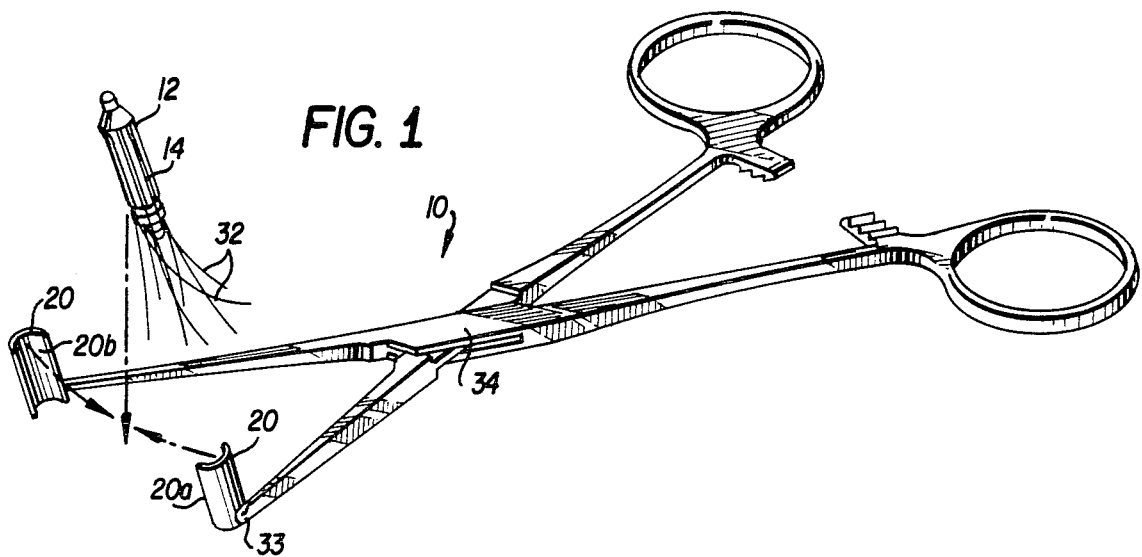
FIG. 1 is an isometric, exploded, view of a suturing assembly of this invention.
Figure 2:
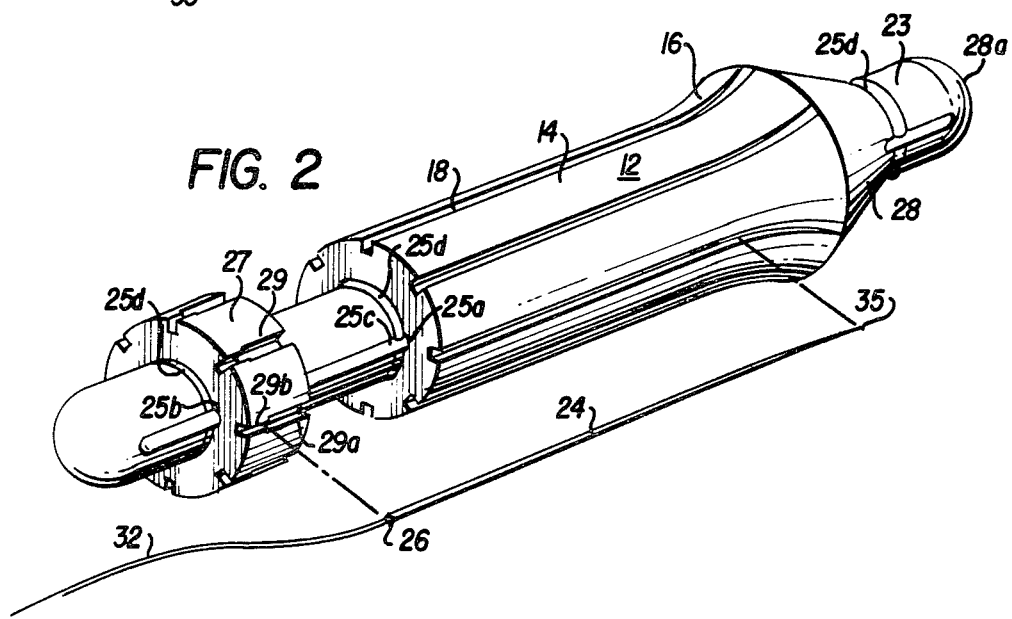
FIG. 2 is an exploded view of a core and needle of the suturing assembly of FIG. 1.

A surgical suturing assembly 10 of this invention comprises a core 12 which has a first, cylindrically, shaped portion 14 and a flared portion 16. The core 12 defines a plurality of longitudinal slots 18 which run along the outer surface of the cylindrically-shaped portion 14 and up the flared portion 16. That is, the slots 18 are continuous between the cylindrically-shaped portion 14 and the flared portion 16 so that they also flare outwardly at the flared portion 16. In a preferred embodiment, the core 12 is constructed of a single piece of metal such as copper, however, other materials could be used as well.

When the assembly 10 is to be used, the cylindrically-shaped portion 14 of the core 12 is surrounded by a tubularly-shaped metallic sleeve 20 which holds a plurality of flexible surgical needles 24 in the slots 18, there being one needle in each slot. Although the sleeve 20 is of such a size and shape that it will prevent the needles 24 from moving radially out of the slots 18, it allows the needles 24 to move longitudinally within the slots so that the needles can be moved toward the flared portion 16.

Figure 3:
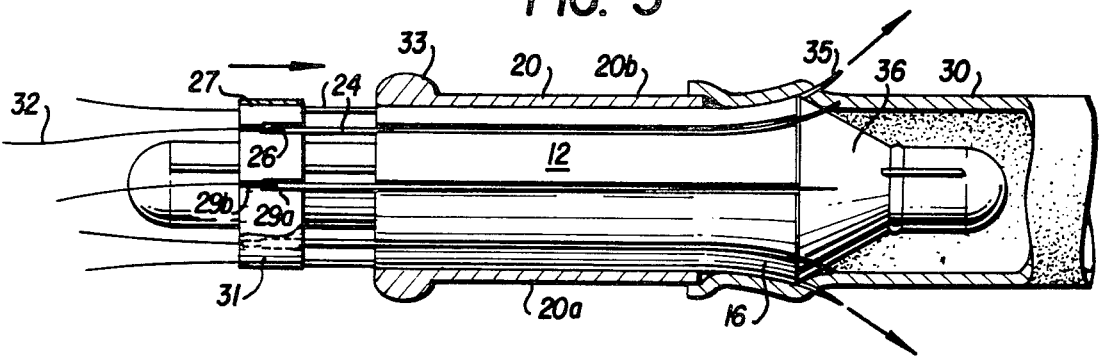
FIG. 3 is a partially-in-section side view of the suturing assembly of FIG. 1 being used to penetrate a blood vessel with a plurality of suture needles.

As can be seen in FIG. 3, when the core 12 is mounted in the sleeve 20, the flared portion 16, being bigger than the sleeve 20, extends outside of the sleeve 20 so that the ends of the slots 18 on the flared portion 16 are outside of the sleeve 20.

The needles 24 are substantially longer than either the sleeve 20 or the cylindrically-shaped portion 14 of the core 12 so that before the assembly is used, the proximal ends 26 of the needles extend outside of the sleeve 20 and core 12 as is shown in FIG. 3.

A cylindrically-shaped cap 27 having slots 29 therein fits over the proximal ends 26 of the needles 24 to aid a surgeon in causing the needles 24 to move longitudinally in the core slots 12. In this respect, the cap slots 29 have larger portions 29a for receiving the needle ends 26 and smaller portions 29b for allowing suture thread 32 attached to the needles 24 to pass through the cap but not the needles 24. The cap 27 is held onto the needles 24 and thread 32 by tape 31 which can easily be removed to free the cap 27 from the needles 24 and thread 32.

The cap 27 and the core 12 are held in proper orientation one to the other by a keyed shaft 23 which slidably passes through bores which extend longitudinally through the core 12 and the cap 27. The bores of each of these members has a slot 25a and 25b respectively which keys with a longitudinal ridge 25c on the shaft 23, thereby maintaining the core 12 and cap 27 in proper angular positions one to the other as they slide longitudinally. The shaft 23 is tightly fitted to the bores of the core 12 and cap 27 so that these members only slide longitudinally on the shaft 23 when sufficient force is applied thereto. In one embodiment small beads 25d are molded onto the shaft 23 to inhibit longitudinal sliding motion of the core 12 and the cap 27 until a sufficient external force causes these members to pass over the beads. The shaft 23 and its beads 25d are molded of plastic, although other materials can be used.

The core 12 and the shaft 23, on the side of the flare 16 opposite the cylindrical portion 14 has a somewhat pointed guide end 28 and 28a which allows a surgeon to more easily insert the flared portion 16 into a blood vessel, or other body duct 30.

As mentioned above, the proximal ends 26 of the flexible needles 24 are each attached to a suture thread 32. In the preferred embodiment, the flexible needles 24 are constructed of spring steel or some other material which bends relatively easily, but yet which springs back to its original shape when an applied force is removed. The material of which the surgical needles is constructed must have sufficient rigidity to maintain a point 35 which can be forced through normal body duct walls, such as blood vessel walls.

In one embodiment, the sleeve 20 is constructed of separable parts 20a and 20b which are held together by a clamp 34. The clamp 34 is of the "scissors" type shown in FIG. 1 to enable a surgeon to easily manipulate the sleeve 20. The two sides of the "scissors" clamp 34 are attached to the sleeve 20 at welds 33. The purpose in making the sleeve 20 of separable parts will be clear from the following description of operation of this assembly 10.

In operation, the pointed guide end 28 of the core 12 is inserted into the end 36 of a duct 30. At this point, using sufficient force on the cap 27, the proximal ends 26 of the needles 24 are pushed longitudinally along the core 12 against the flared portion 16 so that, as they are pushed along, the pointed, distal ends 35 of the needles are temporarily bent outwardly by the flared portion 16 so that the longitudinal movement of the needles forces their pointed tips 35 through the wall of the duct 30, as depicted in FIG. 3. Once all of the needles are through the duct 30, the shaft 23 is removed, the clamp 34 is loosened and the sleeve 20 is removed from the core 12. The core is then pulled from between the needles 24 and their attached threads. Likewise, the cap 27 is removed by removing the tape 31. The needles 24 are then pulled, by hand or with a tool, through the walls of the duct 30.

Figure 4:
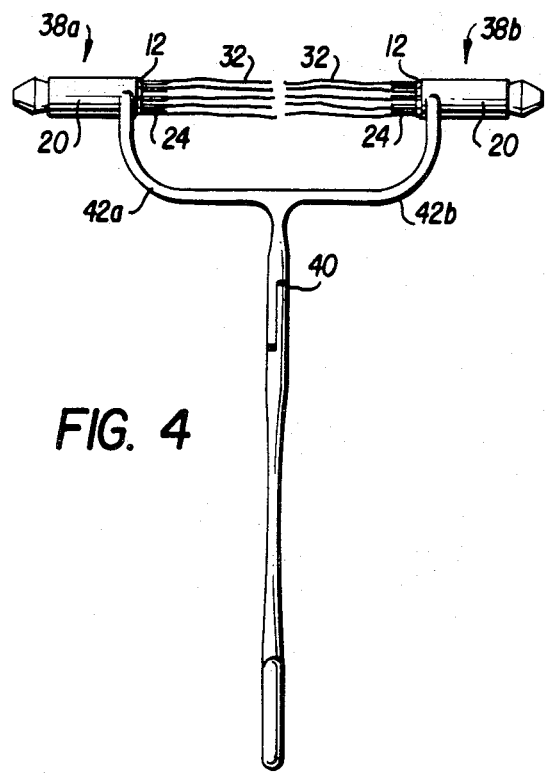
FIG. 4 is a top view of a particular arrangement of the invention.

In a particular arrangement depicted in FIG. 4, there are two identical suturing assemblies 38a and 38b, basically of the type already described, positioned back-to-back, with suturing thread 32 extending between respective needles located at the same respective angular positions. The FIG. 4 embodiment does not employ caps, thus the needles are forced to move longitudinally by hand or an external tool. In this embodiment, a guide extending between the sleeves 20 of the identical assemblies 38a and b to ensure that the assemblies 38a and b remain at the same angular positions is a single clamp 40 having portions 42a and 42b which extend to each of the assemblies. In the use of such a back-to-back arrangement one of the assemblies 38a is used in basically the manner described above to place needles through the wall of a first body duct 44a and the other assembly is used in the manner described above to place needles through the wall of a second body duct 44b.

Figure 5:
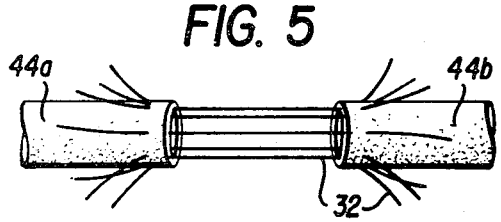
FIG. 5 is an isometric view of two blood vessels which have been penetrated by suturing needles according to the teachings of this invention, but which have not yet been pulled together.
Figure 6:
FIG. 6 is a side view of two blood vessels that have been sewn together by the apparatus and method of this invention.

Once the needles 24 have been forced through the walls of the respective body ducts 44a and b basically in the manner described above, the clamp 40, which, as mentioned above, is common to both of the assemblies, is removed and the two cores are removed so that one is left with the FIG. 5 arrangement. The needles are then pulled through each of the respective body ducts 44a and b by hand and the body ducts are pulled together by the suture threads 32. One then completes the sutures as is depicted in FIG. 6.

Figure 7:
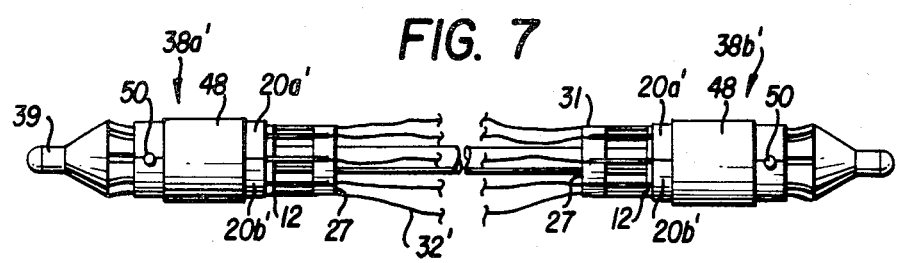
FIG. 7 is a side view of another embodiment of this invention.

A similar embodiment is depicted in FIG. 7 in which tape 48 replaces the clamps which are used in the above described embodiments to hold sleeve halves 20a and 20b together. Threads 32' are color coded to enable a surgeon to readily ascertain when the two assemblies 38a' and 38b' are properly angularly oriented one to the other. The two assemblies 38a' and 38b', including this time caps 27, are also maintained in proper angular orientation by a keyed shaft 39 which extends through bores in the cores 12 and the caps 27. In embodiments such as this one and that of FIG. 4, the threads extending between needles of back-to-back assemblies are about 18 inches long. In this embodiment, once the respective assemblies 38a' and 38b' have been used to insert threads 32' through two opposite blood vessels in the manner described above, the tapes 48 are severed so that sleeve halves 20a' and 20b' can be separated to release the needles, threads and cores 12. Also, cap tapes 31 are severed and the caps 27 are removed. The keyed shaft 39 is removed from the cores 12 and caps 27. Although all of the embodiments described herein can be made to be disposable, this one is more easily adaptable to be disposable because the tape is less expensive than the clamps of other embodiments. The assemblies 38a' and 38b' are assembled on the shaft 39 at a factory and, once they have been used, all parts thereof not used in a suture are discarded.

While the invention has been particularly shown and described with reference to a preferred embodiment, it will be understood by those skilled in the art that various changes in form and detail may be made therein without departing from the spirit and scope of the invention. For example, the assemblies of this invention can be fabricated of many different sizes to fit the many different size blood vessels in the human body for which they will be used. A surgeon could then choose a 1 mm assembly to suture a 1 mm blood vessel, for example. Also, all parts except the suture needles could be molded of plastic. Rather than being keyed, the shaft 23 could be of a polygonal cross-sectional shape to match an indentical bore shape. Further, rather than being held onto the shafts by force fit, the cores and caps could be held on by a high viscosity material such as grease or a frangible cement. In addition, in some cases it may be necessary to employ a keying mechanism between the sleeve 20 and the core 12 to prevent longitudinal relative movement between these members when the needles 24 are urged against the flared portion 16. For example, a short pin 50 extending radially from the core could be positioned in indentations at the abutting edges of sleeve halves 20a and 20b.

It can be appreciated by those skilled in the art that this invention is rather uncomplicated and is not difficult to fabricate. Similarly, the invention is relatively easy to use. But most importantly, the invention literally saves hours of operating-room time by enabling a surgeon to more quickly sew one blood vessel to another. This invention accomplishes this without the use of staples but rather employs commonly used suturing materials which are preferable to metallic and plastic staples and which provide more satisfactory connections and allow living tissue to continue to grow.

The embodiments of the invention in which an exclusive property or privilege are claimed are defined as follows:

1. A surgical suturing assembly especially adapted for use in the rejoining of severed tubular body ducts such as blood vessels and the like comprising:
    a plurality of flexible suture needle means for piercing the walls of said severed tubular body ducts, passing through these walls, and pulling suture material therethrough;
    a core having a first cylindrically-shaped portion defining a plurality of longitudinally oriented slots about the surface thereof and a second flared, slotted, end portion located at the end of said first portion, said second portion, and the slots defined therewith, being continuous with said first portion and its slots such that said slots flare at said flared end portion, each of said slots being of a size for receiving at least one of said needle means, but allowing said needle means freedom for longitudinal movement therein;
    a tubularly shaped sleeve for surrounding said first portion of said core, said sleeve being of a size and shape for holding said needle means radially in said slots when said core first portion is fully received in said sleeve, but for allowing said needle means freedom of longitudinal movement in said slots, said needle means being longer than either of said core first portion or said sleeve;
    whereby said second, flared portion of said core can be inserted into said severed tubular body duct while said needle means are forced to move in said slots longitudinally against said flared end portion and radially outwardly through the walls of said duct.

2. A surgical suturing assembly as in claim 1 wherein said sleeve is constructed of a plurality of separable parts.

3. A surgical suturing assembly as in claim 2 wherein said separable sleeve parts are held together by a releasable holding means.

4. A surgical suturing assembly as in claim 3 wherein said holding means is a scissors-like clamp.

5. A surgical suturing assembly as in claim 1 wherein said sleeve is tape.

6. A surgical suturing assembly as in claim 1 wherein said assembly includes first and second sets, each having a core, a sleeve, and a plurality of needles arranged as recited, there being suturing threads extending between needles of said respective sets.

7. A surgical suturing assembly as in claim 6 wherein said threads are color coded.

8. A surgical suturing assembly as in claim 6 wherein is further included a guiding means extending between said first and second sets for maintaining the cores of said respective sets in proper orientation one to the other.

9. A surgical suturing assembly as in claim 1 wherein said core has a somewhat pointed end on the opposite side of said flared portion from said cylindrically-shaped portion for enabling an operator to more easily insert the core into a body duct.

10. The process of attaching suturing thread to a severed tubular body duct at multiple points about said duct comprising the steps of:
    inserting a flared end of an elongated core into said severed tubular body duct, said elongated core defining a plurality of longitudinally-oriented slots positioned about an outer surface thereof and located adjacent said flared end, each of said slots being of a size for receiving a needle therein, but for allowing said needle freedom for longitudinal movement therein;
    driving a plurality of needles longitudinally along said slots, each needle being in a separate one of said slots and each needle having a distal, pointed end and a proximal end attached to a suturing thread, said distal pointed ends being driven into said severed tubular body duct against said flared surface of said core thereby causing said needles to bend outwardly and be driven through the wall of said tubular body duct at said multiple points; and
    forcing said needles and threads through the wall of said tubular body duct at said multiple points about said severed tubular body duct.

11. A process as recited in claim 10 wherein a portion of said core is surrounded by a tubularly-shaped sleeve to guide said needles longitudinally along said core against said flared portion and through the walls of said body duct.

* * * * *